(12) United States Patent
Tsusaka et al.

(10) Patent No.: US 12,232,748 B2
(45) Date of Patent: Feb. 25, 2025

(54) SURGICAL INSTRUMENT

(71) Applicant: KYOCERA Corporation, Kyoto (JP)

(72) Inventors: Shinya Tsusaka, Osaka (JP); Akinori Mori, Otsu (JP); Masahiko Hashida, Toyonaka (JP)

(73) Assignee: KYOCERA Corporation, Kyoto (JP)

( * ) Notice: Subject to any disclaimer, the term of this patent is extended or adjusted under 35 U.S.C. 154(b) by 347 days.

(21) Appl. No.: 17/598,194

(22) PCT Filed: Mar. 27, 2020

(86) PCT No.: PCT/JP2020/014098
§ 371 (c)(1),
(2) Date: Sep. 24, 2021

(87) PCT Pub. No.: WO2020/203796
PCT Pub. Date: Oct. 8, 2020

(65) Prior Publication Data
US 2022/0183700 A1    Jun. 16, 2022

(30) Foreign Application Priority Data
Mar. 29, 2019    (JP) .................. 2019-067856

(51) Int. Cl.
A61B 17/15    (2006.01)
A61F 2/46    (2006.01)

(52) U.S. Cl.
CPC ............ A61B 17/155 (2013.01); A61F 2/461 (2013.01)

(58) Field of Classification Search
CPC ... A61B 17/155; A61B 17/154; A61B 17/157; A61B 17/1735; A61F 2/461
See application file for complete search history.

(56) References Cited

U.S. PATENT DOCUMENTS 5,486,178 A      1/1996   Hodge
8,313,491 B2 *  11/2012   Green, II ............. A61B 17/155
                                            606/88

(Continued)

FOREIGN PATENT DOCUMENTS

DE    69531184 T2    6/2004
EP    3155989 A1    4/2017

(Continued)

Primary Examiner — Tracy L Kamikawa
(74) Attorney, Agent, or Firm — Procopio, Cory, Hargreaves & Savitch LLP

(57) ABSTRACT

An object of the present disclosure is to provide a surgical instrument that can facilitate adjustment between a progressive position gap and a flexed position gap by additionally resecting a bone after resection of a femur distal portion. A surgical instrument (1) includes a body portion (2) including a first abutment surface (5) abuttable against a distal end resection surface (102) of a femur distal portion (101) and a posterior condyle abutment portion (3) including a second abutment surface (10) abuttable against a posterior condyle resection surface (104) of a posterior condyle portion (103) of a femur (100) and connected to the body portion (2). The body portion (2) includes a first slit (7) extending in a direction parallel to the second abutment surface (10) and a second slit (8) extending in a direction intersecting the first abutment surface (5) and the second abutment surface (10).

10 Claims, 8 Drawing Sheets

(56) References Cited

U.S. PATENT DOCUMENTS

| | | | |
|---|---|---|---|
| 8,506,571 B2 * | 8/2013 | Chana | A61B 17/72 606/88 |
| 8,551,100 B2 * | 10/2013 | Metzger | A61B 17/142 606/87 |
| 2007/0239157 A1 | 10/2007 | Guillaume | |
| 2011/0245835 A1 | 10/2011 | Dodds et al. | |
| 2017/0007273 A1 | 1/2017 | Freiberg et al. | |
| 2017/0333210 A1 * | 11/2017 | Lashure | A61B 17/155 |
| 2018/0228625 A1 * | 8/2018 | Parisi | A61B 17/155 |

FOREIGN PATENT DOCUMENTS

| | | |
|---|---|---|
| FR | 2840797 A1 | 12/2003 |
| JP | 2001-264186 A | 9/2001 |
| JP | 2004-215878 A | 8/2004 |
| JP | 2010-531187 A | 9/2010 |
| JP | 2016-032543 A | 3/2016 |
| JP | 2018-519926 A | 7/2018 |
| WO | 94/00056 A1 | 1/1994 |

* cited by examiner

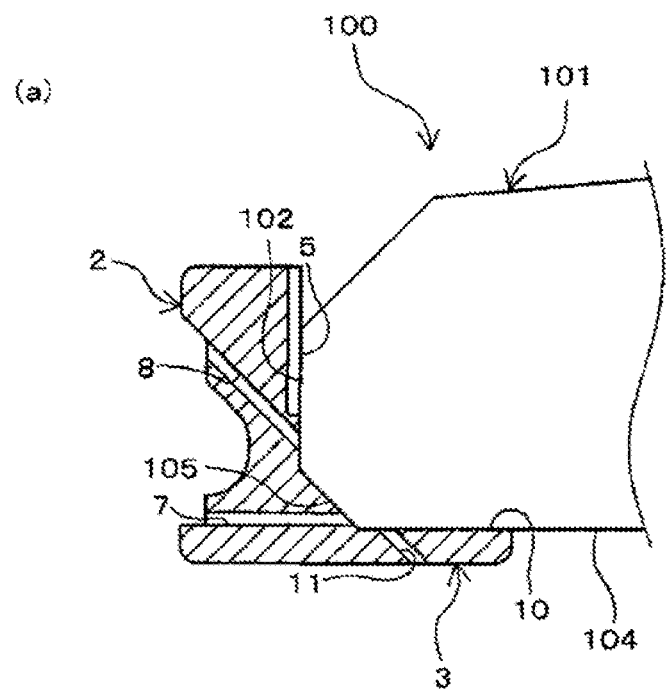
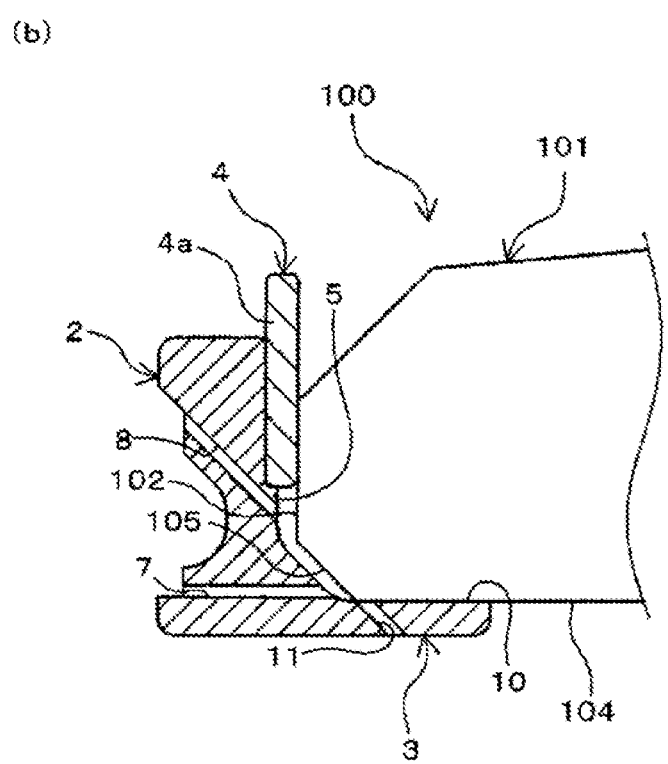
FIG. 8

SURGICAL INSTRUMENT

CROSS REFERENCES TO RELATED APPLICATIONS

This application is a U.S. national application of PCT International Patent Application No. PCT/JP2020/014098, filed on Mar. 27, 2020, which claims the benefit of Japan patent application no. 2019-067856, filed on Mar. 29, 2019.

TECHNICAL FIELD

The present disclosure relates to a surgical instrument for guiding a bone resection instrument for additionally resecting a femur in an artificial knee joint replacement technique.

BACKGROUND ART

In an artificial knee joint replacement technique, in order to achieve smooth bending and stretching of the knee after surgery, in a bending position of the knee, the distance of the gap between a tibial proximal portion and a femur distal portion should be the same in each of a flexed position and an extended position, i.e., an extended position gap and a flexed position gap.

Conventionally, in the artificial knee joint replacement technique, a surgeon first performs osteotomy of a tibial proximal portion in the horizontal direction and osteotomy of a femur distal portion. It is known that after osteotomy of the femur in the artificial knee joint replacement technique, the femur after osteotomy is down-sized by re-resecting the bone. First, in a state in which a femur distal bone resection surface and a chamfer portion bone resection surface of a guide body are brought into close contact with the femur distal portion and a front chamfer portion, a fixing pin is inserted into a locking hole to mount the guide body, and re-resecting of the femur is performed. Next, the fixing pin is removed, and the guide body is turned upside down and is fixed by the fixing pin in a state in which the chamfer portion bone resection surface is brought into close contact with a rear chamfer portion of the femur, and re-resecting of the rear chamfer portion is performed with the bone resection instrument.

SUMMARY

The present disclosure discloses a surgical instrument that is capable of additionally resecting a bone after resection of a femur distal portion to facilitate adjustment between a progressive position gap and a flexed position gap.

Solution to Problem

A surgical instrument according to an aspect of the present disclosure is a surgical instrument for guiding a bone resection instrument for resecting a femur, the surgical instrument including a body portion including a first abutment surface abuttable against a distal end resection surface of a femur distal portion, and a posterior condyle abutment portion including a second abutment surface abuttable against a posterior condyle resection surface of a posterior condyle portion of the femur and connected to the body portion, and the body portion includes a first slit extending in a direction parallel to the second abutment surface, and a second slit extending in a direction intersecting the first abutment surface and the second abutment surface.

Advantageous Effects of Invention

According to the present disclosure, it is possible to provide a surgical instrument that is capable of additionally resecting a bone after resection of a femur distal portion to facilitate adjustment between a progressive position gap and a flexed position gap.

BRIEF DESCRIPTION OF DRAWINGS

FIG. 3(a) is a view illustrating a state in which a position adjustment mechanism is not attached, and FIG. 3(b) is a view illustrating a state in which the position adjustment mechanism is attached.

FIG. 6(a) illustrates a state before the surgical instrument is attached to the femur distal portion, and FIG. 6(b) illustrates a state after the surgical instrument is attached to the femur distal portion.

FIG. 7(a) illustrates a state in which the femur distal portion is additionally resected, and FIG. 7(b) illustrates a state in which the surgical instrument is removed from the femur distal portion after the femur distal portion is additionally resected.

FIG. 8 is a view illustrating a surgical instrument for performing additional resection of the femur distal portion. FIG. 8(a) illustrates a case where the position adjustment mechanism is not attached, and FIG. 8(b) is a view illustrating a case where the position adjustment mechanism is attached.

DESCRIPTION OF EMBODIMENTS

Embodiments of the present disclosure are described below with reference to the drawings. Note that the present disclosure can be broadly applied as a surgical instrument for guiding a bone resection instrument for additionally resecting a femur in an artificial knee joint replacement technique.

Note that, in each of the drawings described below, for convenience of explanation, a direction indicated by an arrow described as "front" is referred to as "forward direction" or "front side", a direction indicated by an arrow described as "rear" is referred to as "rearward direction" or "rear side", a direction indicated by an arrow described as "right" is referred to as "rightward direction", a direction indicated by an arrow described as "left" is referred to as "leftward direction", a direction indicated by an arrow described as "up" is referred to as "upward direction", and a direction indicated by an arrow described as "down" is referred to as "downward direction".

Figure 1:
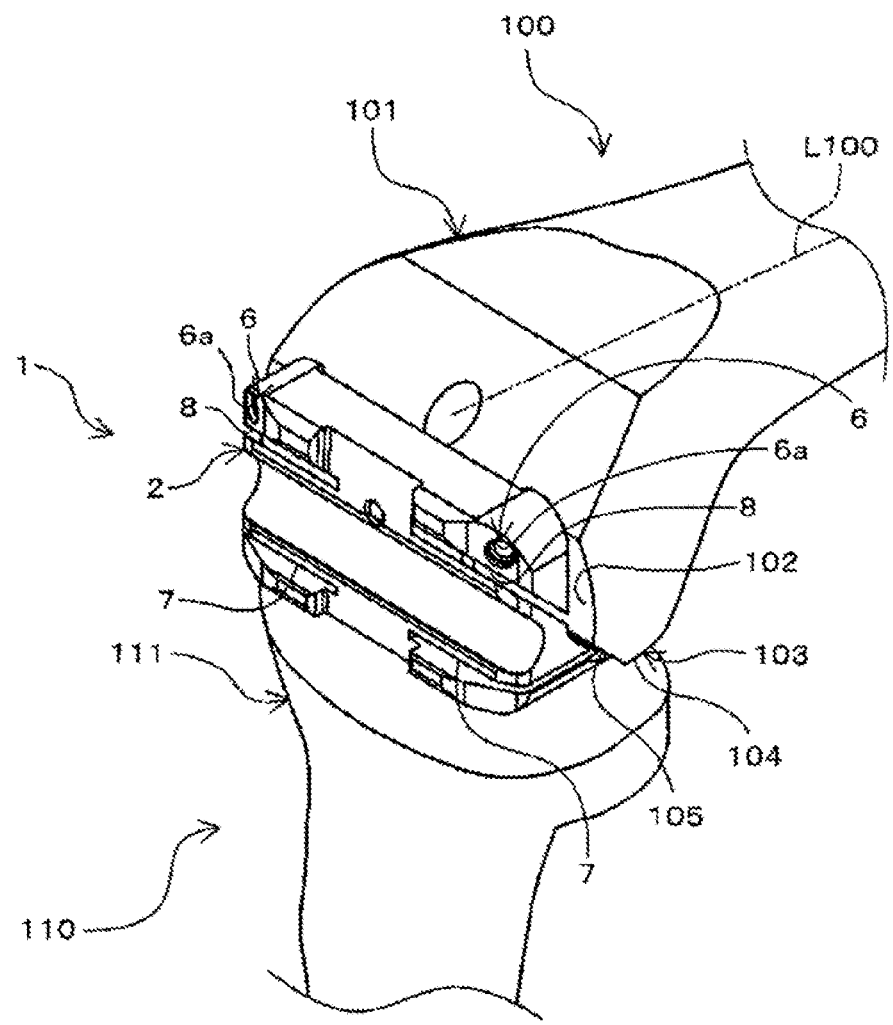
FIG. 1 is a view illustrating a surgical instrument according to one embodiment, and is a perspective view illustrating a state in which the surgical instrument is attached to a femur distal portion in a flexed position.
Figure 2:
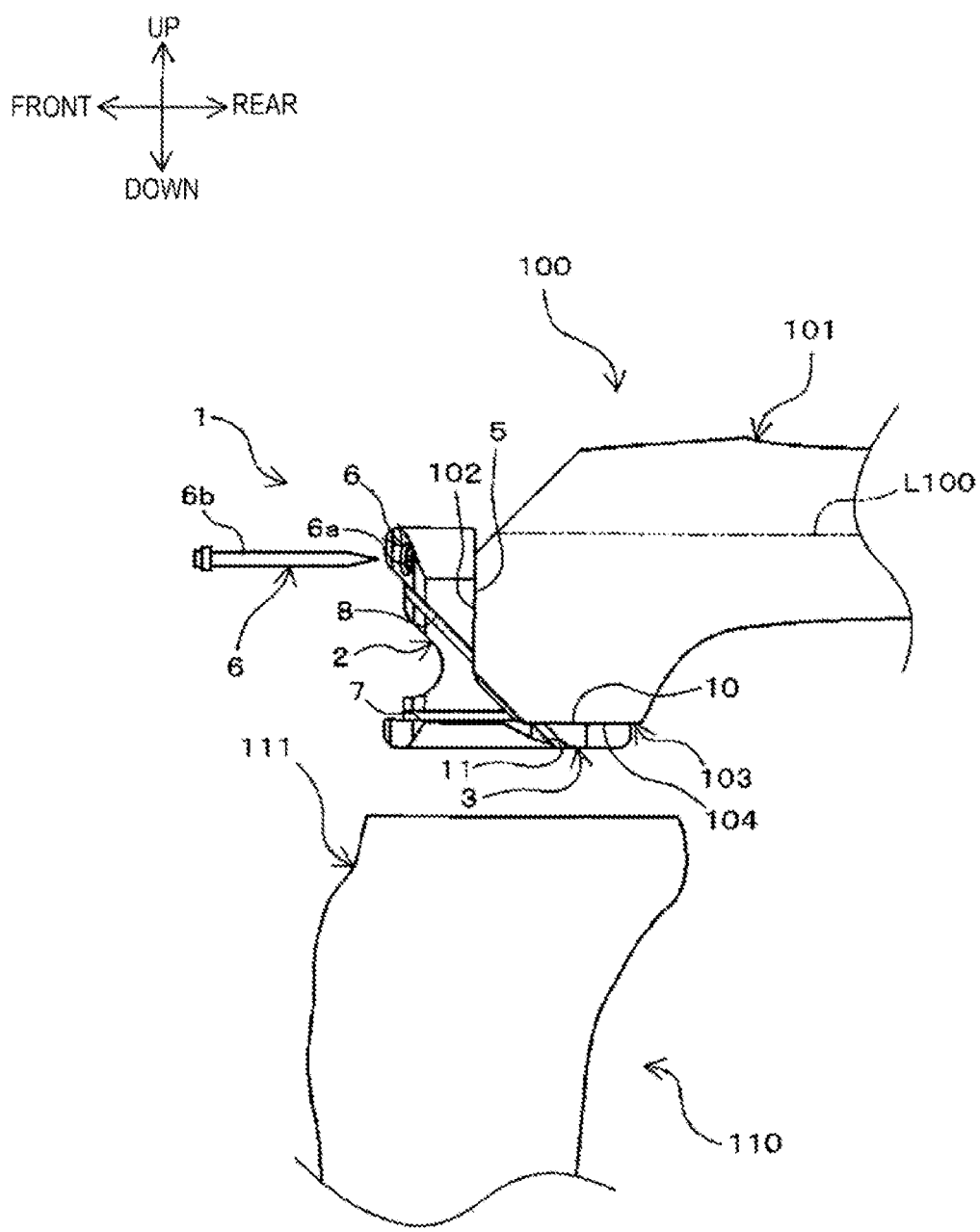
FIG. 2 is a side view illustrating a state in which the surgical instrument illustrated in FIG. 1 is attached to the femur distal portion in the flexed position.

FIG. 1 is a view illustrating a surgical instrument 1 according to one embodiment, and is a perspective view illustrating a state in which the surgical instrument 1 is attached to a femur distal portion 101 in the flexed position. FIG. 2 is a side view illustrating a state in which the surgical instrument 1 illustrated in FIG. 1 is attached to the femur distal portion 101 in the flexed position. Note that in FIG. 1, an illustration of a fixing pin 6b for attaching the surgical instrument 1 to the femur 100 is omitted.

The surgical instrument 1 is an instrument used to guide a bone resection instrument (not illustrated) when additional resection of the femur 100 is performed in an artificial knee joint replacement technique. In the artificial knee joint replacement technique, a resection surface is first formed in the femur distal portion with an instrument different from the surgical instrument 1. At this time, a plurality of resection surfaces are formed in the femur 100. Specifically, at the femur distal portion 101, a distal end resection surface 102 that is a resection surface perpendicular to a bone axis of the femur is formed. A posterior condyle resection surface 104 is formed perpendicular to the distal end resection surface 102 in a posterior condyle portion 103. Further, at least a rear chamfer resection surface 105 that obliquely extends between and relative to the distal end resection surface 102 and the posterior condyle resection surface 104 is formed.

The distal end resection surface 102 is a resection surface in the femur distal portion 101 resected for installing a femur component (not illustrated) of an artificial knee joint, and is formed, for example, as a resection surface perpendicular to a bone axis L100 of the femur. The posterior condyle resection surface 104 is the resection surface of the posterior condyle portion 103 of the femur 100, the posterior condyle portion 103 being formed perpendicular to the distal end resection surface 102. Note that, in accordance with purpose and the like, the distal end resection surface 102 may be formed as a resection surface substantially perpendicular to the bone axis L100 of the femur. For example, the distal end resection surface 102 may be formed inclined from a position perpendicular to the bone axis L100 of the femur, due to a resection error in the osteotomy, correction of a joint surface, and the like.

Figure 3:
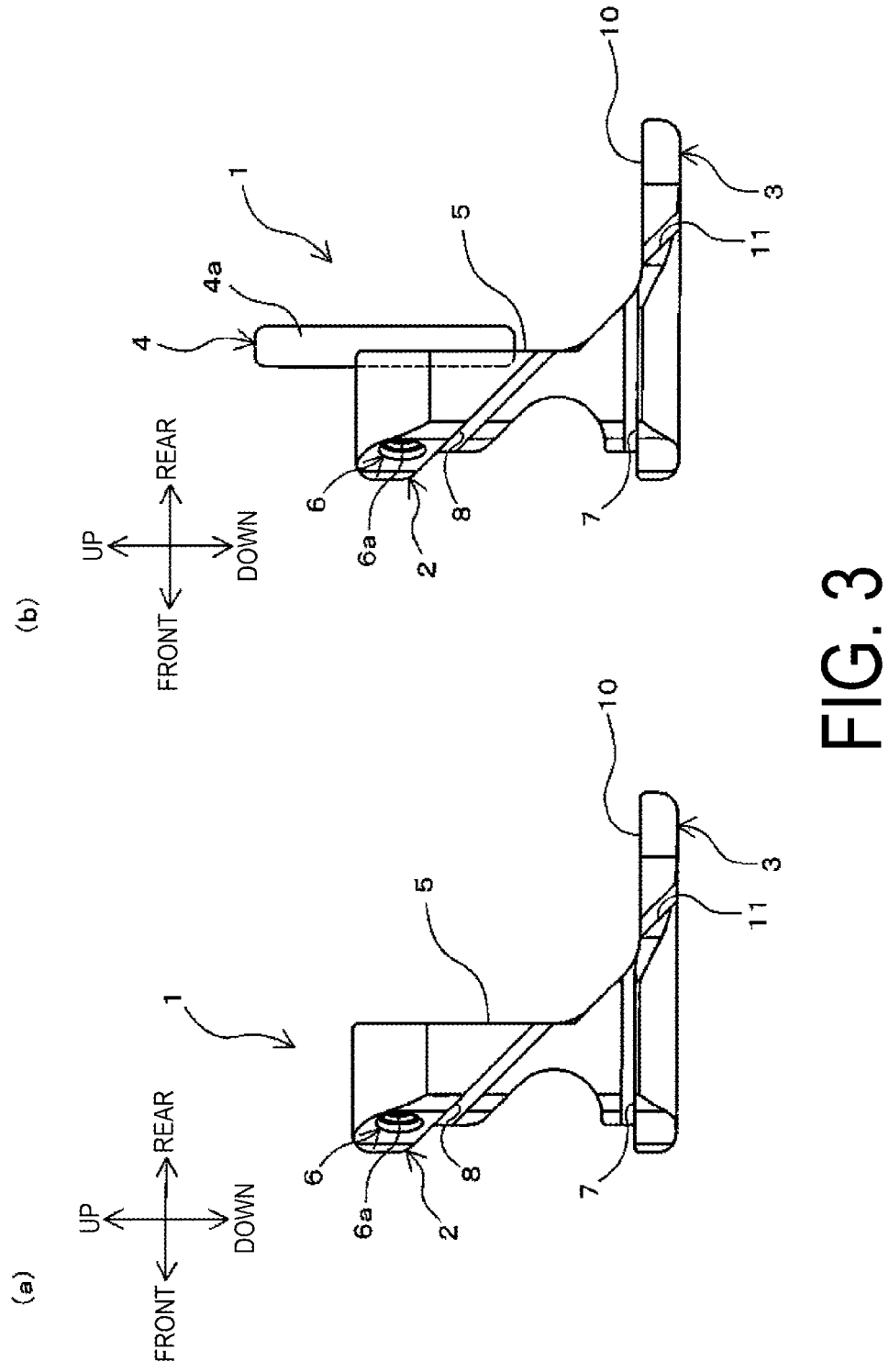
FIG. 3 is a side view illustrating the surgical instrument illustrated in FIG. 2.
Figure 4:
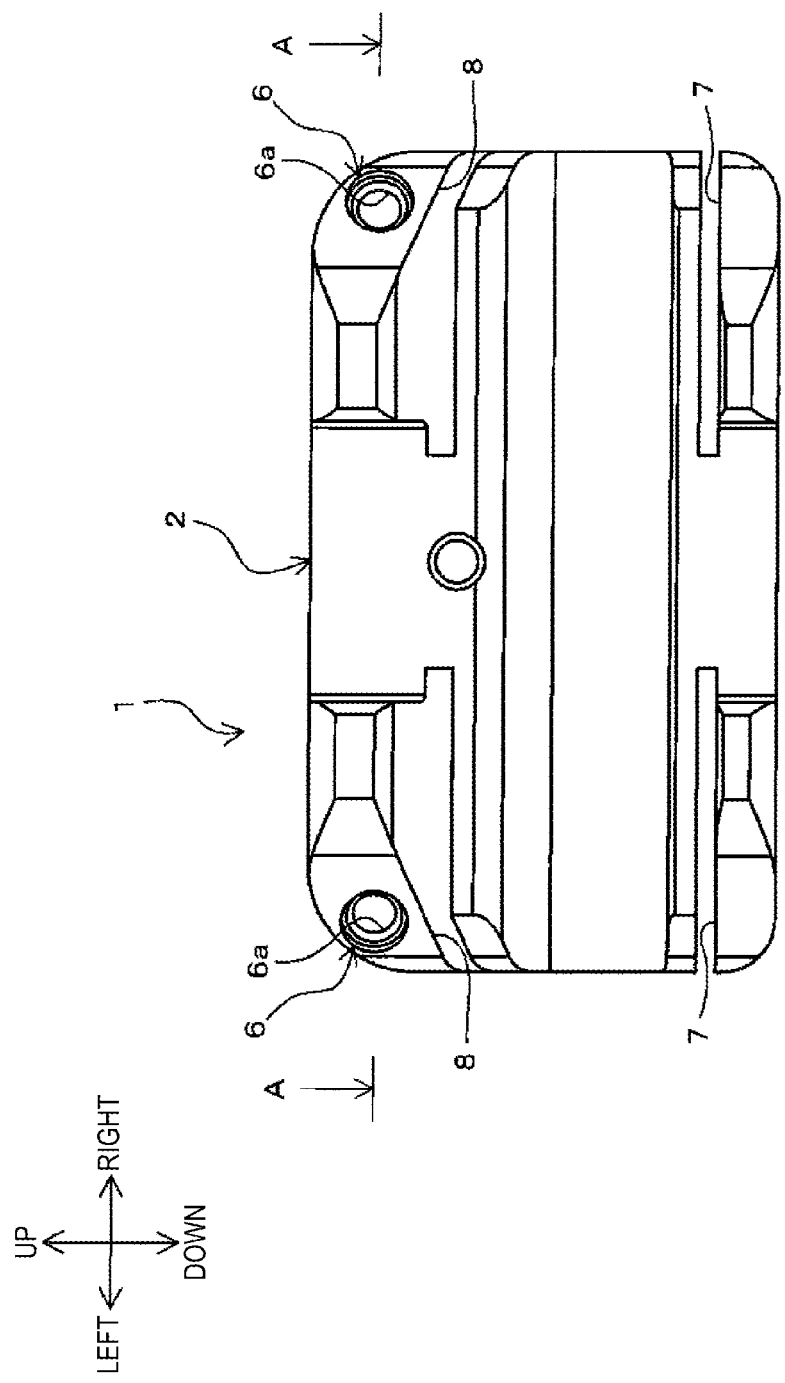
FIG. 4 is a front view illustrating the surgical instrument illustrated in FIG. 3(a).
Figure 5:
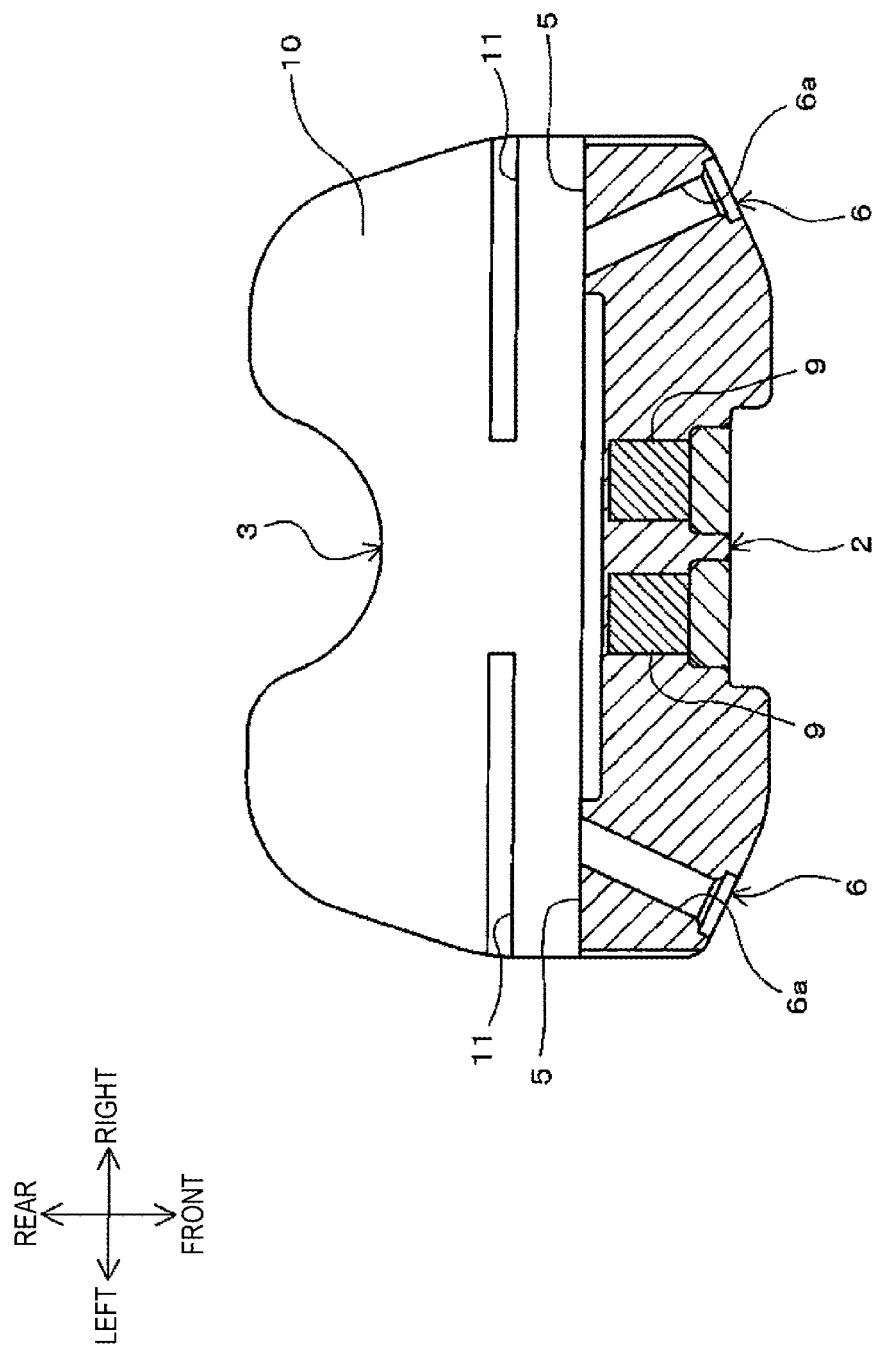
FIG. 5 is a cross-sectional view of the surgical instrument illustrated in FIG. 4 at an A-A line arrowhead position.

FIG. 3 is a side view illustrating the surgical instrument 1 illustrated in FIG. 2. FIG. 3(a) is a view illustrating a state in which a position adjustment mechanism 4 is not attached, and FIG. 3(b) is a view illustrating a state in which the position adjustment mechanism 4 is attached. FIG. 4 is a front view illustrating the surgical instrument 1 illustrated in FIG. 2. FIG. 5 is a cross-sectional view of the surgical instrument 1 illustrated in FIG. 4 at an A-A line arrowhead position. The surgical instrument 1 guides a bone resection instrument to resect the femur when a resection surface of the femur distal portion 101 formed by the osteotomy is to be additionally resected. The surgical instrument 1 includes a body portion 2, a posterior condyle abutment portion 3, and a position adjustment mechanism 4.

As illustrated in FIGS. 1 to 3, the body portion 2 is formed in a substantially plate shape having a predetermined thickness in a front-rear direction, and is disposed so as to abut against the distal end resection surface 102 of the femur distal portion 101. The body portion 2 is fixed to the distal end resection surface 102 by a fixing pin 6b to be described later when the additional resection of the resection surface of the femur distal portion 101 is performed. The shape of the body portion 2 is bilaterally symmetrical. The body portion 2 includes a first abutment surface 5, a fixing mechanism 6, a first slit 7 for guiding the bone resection instrument that additionally resects a posterior condyle portion in a direction parallel to the posterior condyle resection surface 102, a second slit 8 for guiding the bone resection instrument that additionally resects the posterior condyle portion in a direction parallel to the rear chamfer resection surface 105, and a magnetic body 9.

As illustrated in FIGS. 2 and 3, the first abutment surface 5 is a flat surface formed on the rear side of the body portion 2. The first abutment surface 5 is, in the body portion 2, abuttable against the distal end resection surface 102 of the femur 100, the distal end resection surface 102 being formed perpendicular to the bone axis L100 of the femur. The first abutment surface 5 is provided in a direction perpendicular to the posterior condyle resection surface 104.

The fixing mechanism 6 is configured to hold the first abutment surface 5 to the distal end resection surface 102. The fixing mechanism 6 according to the present embodiment includes a pin hole 6a and a fixing pin 6b.

The pin hole 6a is a hole through which the fixing pin 6b to be inserted into the femur is inserted, and is provided as a hole that holds the first abutment surface 5 to the distal end resection surface 102. The pin hole 6a is provided as a through hole that passes through the body portion 2. The fixing pin 6b is inserted into the femur 100 in a state of being inserted through the pin hole 6a. Two pin holes 6a are provided on the upper side of the body portion 2. Each of the fixing pins 6b inserted through the respective pin holes 6a is inserted from the front side. The directions in which the two pin holes 6a pass through the body portion 2 are different from each other. Thus, the fixing pins 6b inserted through the respective pin holes 6a are fixed to the femur distal portion 101 so as to face in different directions from each other.

The first slit 7 is a hole for guiding the bone resection instrument when the additional resection of the posterior condyle resection surface 104 of the femur distal portion 101 is performed. The first slit 7 guides the bone resection instrument that additionally resects the posterior condyle portion 103 in a direction parallel to the posterior condyle resection surface 104. The first slit 7 is formed so as to be parallel to the posterior condyle resection surface 104 when the surgical instrument 1 is installed on the femur distal portion 101. The first slits 7 are formed at two, right and left, locations on the lower side of the body portion 2. The first slit 7 formed on the right side of the body portion 2 is formed so as to be open in the front-rear direction and the rightward direction. The first slit 7 formed on the left side of the body portion 2 is formed so as to be open in the front-rear direction and the leftward direction.

The second slit 8 is a hole for guiding the bone resection instrument when the additional resection of the rear chamfer resection surface 105 of the femur 100 is performed. The second slit 8 guides the bone resection instrument for additionally resecting the posterior condyle portion 103 in a direction parallel to the rear chamfer resection surface 105. In other words, the second slit 8 is formed so as to be parallel to the rear chamfer resection surface 105. The second slit 8 is formed at two, right and left, locations of the body portion 2. Each of the second slits 8 is formed as a hole diagonally passing through the body portion 2 in the front-rear direction. Each of the second slits 8 is inclined downward from the front toward the rear.

The magnetic body 9 is provided for detachably attaching the position adjustment mechanism 4 to the first abutment surface 5 of the body portion 2. The magnetic body 9 is formed in a substantially cylindrical shape. Two magnetic bodies 9 are provided inside the body portion 2, and are disposed substantially in the center in the right-left direction. Each of the magnetic bodies 9 is a permanent magnet such as, for example, a rare earth magnet.

As illustrated in FIGS. 1 to 3, the posterior condyle abutment portion 3 is formed in a substantially plate shape having a predetermined thickness in the vertical direction. The posterior condyle abutment portion 3 extends in a direction perpendicular to the body portion 2. The posterior condyle abutment portion 3 is provided integrally with the body portion 2. The posterior condyle abutment portion 3 extends rearward in a cantilevered manner at the lower end of the body portion 2. The posterior condyle abutment portion 3 is disposed in a gap between a tibial proximal portion 111 of a tibia 110 and the femur distal portion 101. More specifically, the posterior condyle abutment portion 3 is disposed in a state of abutting against the posterior condyle resection surface 104, between the tibial proximal portion 111 and the posterior condyle portion 103 of the femur 100 in the flexed position. The posterior condyle abutment portion 3 includes a second abutment surface 10 and a third slit 11.

The second abutment surface 10 is directly abuttable against the posterior condyle resection surface 104 of the femur 100. The second abutment surface 10 is a flat surface provided on the upper surface of the posterior condyle abutment portion 3. The second abutment surface 10 is configured as a surface perpendicular to the first abutment surface 5 of the body portion 2.

The third slit 11 is a hole provided such that the bone resection instrument guided by the second slit 8 for additionally resecting the rear chamfer resection surface 105 does not abut against the posterior condyle abutment portion 3. The third slit 11 is formed in the posterior condyle abutment portion 3, and is disposed on an extension line of the second slit 8. The third slit 11 is formed parallel to the second slit 8 and the rear chamfer resection surface 105.

The position adjustment mechanism 4 is a member for adjusting the resection position of the femur distal portion 101. The position adjustment mechanism 4 is capable of displacing a holding position of the first abutment surface 5 with respect to the distal end resection surface 102. The position adjustment mechanism 4 according to the present embodiment is configured as an additional spacer 4a.

The additional spacer 4a is detachably attached to the first abutment surface 5 of the body portion 2. The additional spacer 4a in a state of being attached to the first abutment surface 5 is configured to abut against the distal end resection surface 102 of the femur 100. In other words, in a case where the additional spacer 4a is attached to the first abutment surface 5 of the body portion 2, the distal end resection surface 102 of the femur 100 abuts against the additional spacer 4a, and does not directly abut against the first abutment surface 5. In a case where the additional spacer 4a is attached, the body portion 2 is installed on the distal end resection surface 102 via the additional spacer 4a.

The additional spacer 4a is formed in a flat plate shape. At least the front surface and the rear surface of the additional spacer 4a are formed parallel to each other. The additional spacer 4a is a material attracted by a magnetic force, in other words, a ferromagnetic body, and, for example, iron, stainless steel, or the like is used. The additional spacer 4a is detachably attached, with a magnetic force, to the body portion 2 in which the magnet is provided. One additional spacer 4a in the present embodiment is attached to the first abutment surface 5 of the body portion 2. Furthermore, a plurality of additional spacers having thicknesses different from each other may be provided, and the additional spacers can be used, for example, by replacing one additional spacer 4a with another additional spacer 4a having a different thickness depending on the amount of bone resection of the additional resection. As a result, the surgeon can adjust the amount of bone resection of the rear chamfer resection surface.

Additional Resection Step

Figure 6:
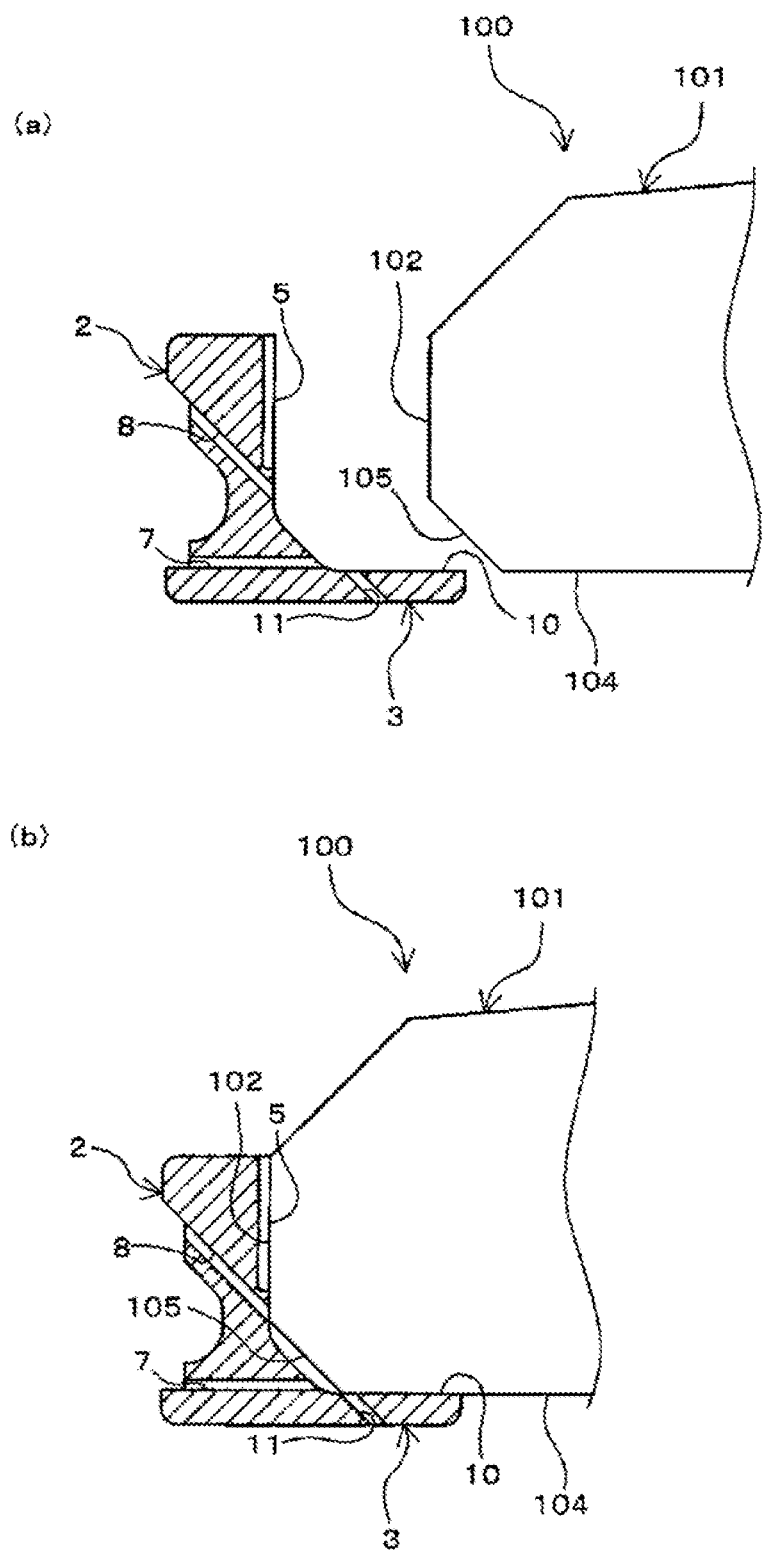
FIG. 6 is a view illustrating a step of additionally resecting the femur distal portion.
Figure 7:
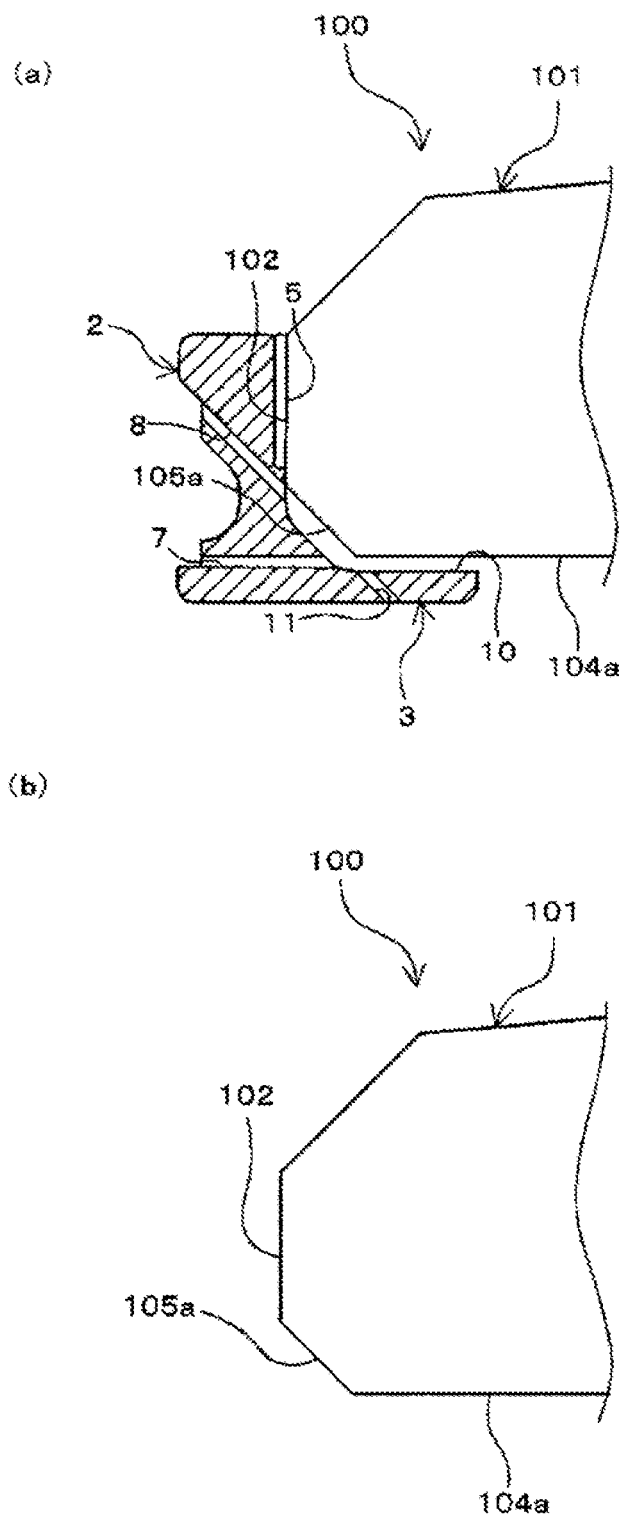
FIG. 7 is a view illustrating a step of additionally resecting the femur distal portion.

FIG. 6 is a view illustrating a step of additionally resecting the femur distal portion 101. FIG. 6(a) illustrates a state before the surgical instrument 1 is attached to the femur distal portion 101, and FIG. 6(b) illustrates a state after the surgical instrument 1 is attached to the femur distal portion 101. FIG. 7 is a view illustrating a step of additionally resecting the femur distal portion. FIG. 7(a) illustrates a state in which the femur distal portion is additionally resected, and FIG. 7(b) illustrates a state in which the surgical instrument is removed from the femur distal portion after additional resection. Note that, in FIGS. 6 and 7, the femur 100 is illustrated in outline and the surgical instrument 1 is illustrated in cross-section. In FIGS. 6 and 7, illustration of the fixing pin 6b is omitted.

In the artificial knee joint replacement technique, the surgeon first performs osteotomy of the tibial proximal portion 111 in the horizontal direction and osteotomy of the femur distal portion 101. The femur distal portion 101 on which the osteotomy is performed is in a state in which a plurality of resection surfaces including the posterior condyle resection surface 104, the distal end resection surface 102, and the rear chamfer resection surface 105 have been formed, as illustrated in FIG. 6(a). Next, as illustrated in FIG. 6(b), the second abutment surface 10 of the posterior condyle abutment portion 3 is abutted against the posterior condyle resection surface 104, and the first abutment surface 5 is abutted against the distal end resection surface 102 by the surgeon. The surgeon then fixes the surgical instrument 1 to the femur 100 with the fixing pin 6b in a state in which the surgical instrument 1 abuts against the femur distal portion 101. As a result, when the surgeon performs the additional resection, the surgical instrument will not inadvertently swing. Thus, the additional resection can be performed in a state in which the surgical instrument is stably fixed to the femur.

Next, as illustrated in FIG. 7(a), the rear chamfer resection surface 105 of the femur distal portion 101 is additionally resected by the bone resection instrument guided by the second slit 8 of the body portion 2. An additionally resected rear chamfer resection surface 105a is formed on the resection surface after the rear chamfer resection surface 105 is additionally resected. Furthermore, the posterior condyle resection surface 104 of the femur distal portion 101 is additionally resected by the bone resection instrument guided by the first slit 7 of the body portion 2. An additionally resected posterior condyle resection surface 104a is formed on the resection surface after the posterior condyle resection surface 104 is additionally resected.

After the rear chamfer resection surface 105 and the posterior condyle resection surface 104 are additionally resected, the surgical instrument 1 is removed from the femur distal portion 101. The femur distal portion 101 with the surgical instrument 1 being removed has a shape as illustrated in FIG. 7(b). The flexed position gap increases due to the additional resection, and the difference between the extended position gap and the flexed position gap is adjusted. Furthermore, as a result of the additional resection of the rear chamfer resection surface 105, the femur distal portion 101 is formed in a state in which the femur component can be attached.

FIG. 8 is a view illustrating the surgical instrument 1 for performing the additional resection of the femur distal portion 101. FIG. 8(a) illustrates a case where the additional spacer 4a is not attached, and FIG. 8(b) is a view illustrating a case where the additional spacer 4a is attached. Note that in FIG. 8, the femur 100 is illustrated in outline and the surgical instrument 1 is illustrated in cross-section. In FIG. 8, an illustration of the fixing pin 6b for attaching the surgical instrument 1 to the femur 100 is omitted.

In the artificial knee joint replacement technique, an appropriately sized instrument is first used to form a resection surface of the femur 100 with dimensions tailored to the individual patient. As for the surgical instrument 1 that performs additional resection after a resection surface is formed, the surgical instrument 1 having a size corresponding to the instrument that is used in forming the resection surface is also used. However, for example, in a case where an instrument for forming a resection surface of a small femur distal portion 101 is used, when the rear chamfer resection surface 105 is additionally resected with a large surgical instrument 1 that does not correspond to the above case, the rear chamfer resection surface 105 is resected by an amount more than the required resection amount, as illustrated in FIG. 8(a). In a case where an instrument for forming a resection surface of a large femur distal portion 101 is used, when the rear chamfer resection surface 105 is additionally resected with a small surgical instrument 1 that does not correspond to the above case, the rear chamfer resection surface 105 is resected by an amount less than the required resection amount.

The additional spacer 4a is the position adjustment mechanism, and is attached to the first abutment surface 5 of the body portion 2, so that the relative position of the second slit 8 with respect to the rear chamfer resection surface 105 can be adjusted. For example, as illustrated in FIG. 8(b), by attaching the additional spacer 4a, the position of the first abutment surface 5 with respect to the distal end resection surface 102 is further spaced apart than that in a case where the additional spacer 4a is not attached, so that the resection position of the second slit 8 with respect to the rear chamfer resection surface 105 can be moved to a position where the resection amount is smaller. In other words, without replacing the surgical instrument 1 and changing the size of the surgical instrument 1 itself, the surgeon can perform resection of the rear chamfer resection surface 105 with an appropriate resection amount by attaching and detaching the additional spacer 4a. As a result, furthermore, the adjustment between the progressive position gap and the flexed position gap can be performed easily.

Effects of Embodiment

The surgical instrument 1 in the present embodiment includes the body portion 2 and the posterior condyle abutment portion 3. The body portion 2 includes the first abutment surface 5 abuttable against the distal end resection surface 102 of the femur 100, and the posterior condyle abutment portion 3 includes the second abutment surface 10 abuttable against the posterior condyle resection surface 104 of the femur 100. The body portion 2 includes the first slit 7 for resecting the posterior condyle portion 103 in a direction parallel to the posterior condyle resection surface 104 and the second slit 8 for resecting the posterior condyle portion 103 in a direction parallel to the rear chamfer resection surface 105. Thus, the surgeon can perform additional resection while the second abutment surface 10 of the surgical instrument 1 is abutted against the posterior condyle resection surface 104 after osteotomy of the femur distal portion 101 when additionally resecting the posterior condyle portion 103 of the femur 100 in the artificial knee joint replacement technique. In other words, the surgeon can perform additional resection at a targeted location with respect to the second abutment surface 10 when resecting the posterior condyle resection surface 104 and the rear chamfer resection surface 105 of the femur distal portion 101. As a result, the surgeon can perform additional resection of the posterior condyle portion 103 in a size required for the resection by adjusting the position of the surgical instrument 1 with respect to the second abutment surface 10 so that the extended position gap and the flexed position gap are the same.

Accordingly, the adjustment between the progressive position gap and the flexed position gap can be facilitated by additionally resecting the bone after the resection of the femur distal portion 101.

According to the surgical instrument 1 of the present embodiment, the first abutment surface 5 can be held to the distal end resection surface 102 by the fixing mechanism 6. Thus, the body portion 2 is fixed to the femur 100, so that the surgical instrument 1 will not inadvertently swing when the additional resection is performed. As a result, the surgeon can perform the additional resection in a state in which the surgical instrument 1 is stably fixed to the femur 100.

According to the surgical instrument 1 of the present embodiment, the fixing mechanism 6 is configured to include the fixing pin 6b and the pin hole 6a through which the fixing pin 6b is inserted. Thus, the first abutment surface 5 is held to the distal end resection surface 102 by the fixing pin 6b inserted through the pin hole 6a and inserted into the femur 100. In other words, the fixing mechanism 6 can be realized with a simple configuration, and the body portion 2 can be fixed to the femur distal portion 101 in a state of being firmly stable.

According to the surgical instrument 1 of the present embodiment, the surgical instrument 1 includes the position adjustment mechanism 4 that is capable of adjusting the holding position of the first abutment surface 5 with respect to the distal end resection surface 102. Thus, the surgeon can adjust the position of the second slit 8 relative to the femur distal portion 101 by the position adjustment mechanism 4. In other words, the surgeon can adjust the amount of bone resection without replacing the surgical instrument 1.

According to the surgical instrument 1 of the present embodiment, the additional spacer 4a can be attached to the first abutment surface 5 of the body portion 2, and, furthermore, the body portion 2 abuts against the distal end resection surface 102 in a state of including the additional spacer 4a. As a result, the first abutment surface 5 of the body portion 2 can be held spaced apart from the femur distal portion 101 by the amount of the additional spacer 4a, and the position of the second slit 8 with respect to the femur distal portion 101 can be adjusted. In other words, the surgeon can adjust the amount of bone resection by merely attaching the additional spacer 4a to the body portion 2 without replacing the surgical instrument 1.

According to the surgical instrument 1 of the present embodiment, at least one of the body portion 2 and/or the additional spacer 4a of the surgical instrument 1 includes the magnetic body, and the additional spacer 4a is detachably attached to the body portion 2. Thus, the surgeon using the surgical instrument 1 can attach and detach the additional spacer 4a to the body portion 2 to easily adjust the amount of bone resection of the femur 100.

Modification Examples

The embodiments of the present disclosure have been described above, but the present disclosure is not limited to the embodiments described above, and can be implemented with various modifications as long as they are described in the claims. For example, the following modification examples may be implemented.

(1) In the above-described embodiment, the case where the fixing mechanism 6 includes the pin hole 6a and the fixing pin 6b has been described as an example, but this need not be the case. For example, the fixing mechanism 6 may be provided in the body portion 2 as a locking part that is capable of being locked to the femur 100.

(2) In the above-described embodiment, the case where two pin holes 6a are provided in the body portion 2 has been described as an example, but this need not be the case. For example, three or more pin holes 6a may be provided.

(3) In the above-described embodiment, the case where the additional spacer 4a is used as the position adjustment mechanism 4 has been described as an example, but this need not be the case. For example, the position adjustment mechanism 4 may include a sliding portion that slidably holds the first abutment surface 5 of the body portion 2 in the direction of the bone axis L100 of the femur.

(4) In the above-described embodiment, the case where the body portion 2 includes the magnetic body 9 has been described as an example, but this need not be the case. For example, the additional spacer 4a may include the magnetic body 9, and the body portion 2 may use a material attracted by a magnetic force.

(5) In the above-described embodiment, the case where the magnetic body 9 is provided only inside the body portion 2 has been described as an example, but this need not be the case. For example, the magnetic body 9 may be provided not only in the body portion 2 but also in the additional spacer 4a, and the poles of the magnetic bodies 9 in the body portion 2 and the additional spacer 4a are disposed to be opposite to each other so as to be configured to be attracted each other.

(6) In the above-described embodiments, the case where the additional spacer 4a is attached and detached by a magnetic force to and from the first abutment surface 5 of the body portion 2 has been described as an example, but this need not be the case. For example, the additional spacer 4a may be mechanically attachable and detachable, for example, by being fitted to the first abutment surface 5 of the body portion 2 by sliding.

(7) In the above-described embodiments, the case where one additional spacer 4a is attached to the first abutment surface 5 of the body portion 2 and the position adjustment is performed has been described as an example, but this need not be the case. For example, a plurality of the additional spacers 4a may be configured to be attached to the first abutment surface 5 of the body portion 2.

Conclusion (1) A surgical instrument 1 according to an aspect of the present disclosure is the surgical instrument 1 for guiding a bone resection instrument that resects a femur 100, the surgical instrument 1 including a body portion 2 provided with a first abutment surface 5 abuttable against a distal end resection surface 102 that is a resection surface in a femur distal portion 101 and is a resection surface perpendicular to a bone axis of the femur 100, and a posterior condyle abutment portion 3 provided to be perpendicular to the first abutment surface 5, including a second abutment surface 10 abuttable against a posterior condyle resection surface 104 that is a resection surface of a posterior condyle portion 103 of the femur 100, and integrally provided with the body portion 2, in which the body portion 2 is provided with a first slit 7 for guiding the bone resection instrument that additionally resects the posterior condyle portion 103 in a direction parallel to the posterior condyle resection surface 104 and a second slit 8 for guiding the bone resection instrument that additionally resects the posterior condyle portion 103 in a direction parallel to a rear chamfer resection surface 105 that is formed to obliquely extend between and relative to the distal end resection surface 102 and the posterior condyle resection surface 104 in the femur 100.

According to the above-described configuration, the surgical instrument 1 includes the body portion 2 and the posterior condyle abutment portion 3. The body portion 2 includes the first abutment surface 5 abuttable against the distal end resection surface 102 of the femur 100, and the posterior condyle abutment portion 3 includes the second abutment surface 10 abuttable against the posterior condyle resection surface 104 of the femur 100. The body portion 2 includes the first slit 7 for resecting the posterior condyle portion 103 in a direction parallel to the posterior condyle resection surface 104 and the second slit 8 for resecting the posterior condyle portion 103 in a direction parallel to the rear chamfer resection surface 105. Thus, the surgeon can perform additional resection while the second abutment surface 10 of the surgical instrument 1 is abutted against the posterior condyle resection surface 104 after osteotomy of the femur distal portion 101 when additionally resecting the posterior condyle portion 103 of the femur 100 in the artificial knee joint replacement technique. In other words, the surgeon can perform additional resection at a targeted location with respect to the second abutment surface 10 when resecting the posterior condyle resection surface 104 and the rear chamfer resection surface 105 of the femur distal portion 101. As a result, the surgeon can perform additional resection of the posterior condyle portion 103 in a size required for the resection by adjusting the position of the surgical instrument 1 with respect to the second abutment surface 10 so that the extended position gap and the flexed position gap are the same.

Accordingly, the adjustment between the progressive position gap and the flexed position gap can be facilitated by additionally resecting the bone after the resection of the femur distal portion 101.

(2) The surgical instrument 1 further includes the fixing mechanism 6 for holding the first abutment surface 5 to the distal end resection surface 102.

In this configuration, the first abutment surface 5 can be held on the distal end resection surface 102 by the fixing mechanism 6. Thus, the body portion 2 is fixed to the femur 100, so that the surgical instrument 1 will not inadvertently swing when the additional resection is performed. As a result, the surgeon can perform the additional resection in a state in which the surgical instrument 1 is stably fixed to the femur 100.

(3) The fixing mechanism 6 includes the fixing pin 6b inserted into the femur 100 and the pin hole 6a that is provided as a through hole passing through the body portion 2 and into which the fixing pin 6b is inserted, and is configured to hold the first abutment surface 5 to the distal end resection surface 102 through insertion of the fixing pin 6b into the femur 100 in a state in which the fixing pin 6b is inserted into the pin hole 6a.

In this configuration, the fixing mechanism 6 is configured to include the fixing pin 6b and the pin hole 6a through which the fixing pin 6b is inserted. Thus, the first abutment surface 5 is held to the distal end resection surface 102 by the fixing pin 6b inserted through the pin hole 6a and inserted into the femur 100. In other words, the fixing mechanism 6 can be realized with a simple configuration, and the body portion 2 can be fixed to the femur distal portion 101 in a state of being firmly stable.

(4) The surgical instrument 1 includes a plurality of the pin holes 6a, and directions in which the pin holes pass through the body portion 2 are different from each another.

In this configuration, the body portion 2 can be fixed to the femur 100 even better.

(5) The surgical instrument 1 further includes the position adjustment mechanism 4 that is capable of displacing the holding position of the first abutment surface 5 with respect to the distal end resection surface 102.

In this configuration, the surgical instrument 1 includes the position adjustment mechanism 4 that is capable of adjusting the holding position of the first abutment surface 5 with respect to the distal end resection surface 102. Thus, the surgeon can adjust the position of the second slit 8 relative to the femur distal portion 101 by the position adjustment mechanism 4. In other words, the surgeon can adjust the amount of bone resection without replacing the surgical instrument 1.

(6) The position adjustment mechanism 4 is the additional spacer 4a that is configured to be detachably attached to the body portion 2 on the first abutment surface 5 and abut against the distal end resection surface 102 in a state of being attached to the body portion 2.

In this configuration, the additional spacer 4a can be attached to the first abutment surface 5 of the body portion 2, and further the body portion 2 abuts against the distal end resection surface 102 in a state of including the additional spacer 4a. As a result, the first abutment surface 5 of the body portion 2 can be held spaced apart from the femur distal portion 101 by the amount of the additional spacer 4a, and the position of the second slit 8 with respect to the femur distal portion 101 can be adjusted. In other words, the surgeon can adjust the amount of bone resection by merely attaching the additional spacer 4a to the body portion 2 without replacing the surgical instrument 1.

(7) At least one of the body portion 2 and/or the additional spacer 4a includes the magnetic body 9, and the additional spacer 4a is detachably attached to the body portion 2 with a magnetic force.

In this configuration, at least one of the body portion 2 and/or the additional spacer 4a of the surgical instrument 1 includes the magnetic body 9, and the additional spacer 4a is detachably attached to the body portion 2. Thus, the surgeon using the surgical instrument 1 can attach and detach the additional spacer 4a to the body portion 2 to easily adjust the amount of bone resection of the femur 100.

(8) The body portion 2 includes a magnet, and the additional spacer 4a includes a ferromagnetic body and is detachably attached to the body portion 2 with a magnetic force.

In this configuration, a magnet that generates a sufficient magnetic force inside the body portion 2 is provided, so that the additional spacer 4a including a ferromagnetic body such as iron or stainless steel can be reliably attached to the body portion 2. As a result, the manufacturing of the additional spacer 4a is also facilitated.

(9) The surgical instrument 1 includes a plurality of the additional spacers having thicknesses different from each other.

In this configuration, the spacer can be used, for example, by replacing one additional spacer 4a with another additional spacer 4a having a different thickness depending on the amount of bone resection of the additional resection. As a result, the surgeon can easily adjust the amount of bone resection of the rear chamfer resection surface.

(10) The surgical instrument 1 can be used for bone re-resecting for installing a femur side component in the artificial knee joint replacement technique.

INDUSTRIAL APPLICABILITY

The present disclosure can be broadly applied as a surgical instrument for guiding a bone resection instrument for additionally resecting a femur in an artificial knee joint replacement technique.

REFERENCE SIGNS LIST

1 Surgical instrument
2 Body portion
3 Posterior condyle abutment portion
4 Position adjustment mechanism
4a Additional spacer
5 First abutment surface
6 Fixing mechanism
6a Pin hole
6b Fixing pin
7 First slit
8 Second slit
10 Second abutment surface
100 Femur
101 Femur distal portion
102 Distal end resection surface
103 Post condyle portion
104 Posterior condyle resection surface
105 Rear chamfer resection surface
L100 Bone axis of femur

The invention claimed is:
1. A surgical instrument for guiding a bone resection instrument for resecting a femur, the surgical instrument comprising:
 a body including
  a distal body portion comprising a first abutment surface configured to abut against a distal end resection surface of a femur distal portion, the distal body portion having a substantially plate shape; and
  a posterior condyle abutment portion comprising a second abutment surface configured to abut against a posterior condyle resection surface of a posterior condyle portion of the femur and connected to the distal body portion such that the posterior condyle abutment portion extends from a lower end of the distal body portion along the posterior condyle resection surface; and
 a spacer capable of displacing a holding position of the first abutment surface with respect to the distal end resection surface, the spacer being positioned between the distal end resection surface and the distal body portion, wherein
 the body comprises
 a first cutting slit extending in a direction parallel to the second abutment surface, and
 a second cutting slit extending in a direction intersecting the first abutment surface and the second abutment surface,
 wherein when the spacer is attached to the distal body portion, the second slit is disposed between the spacer and the first slit and the spacer protrudes anteriorly past the entire body, along the first abutment surface, in a direction away from the posterior condyle abutment portion.

2. The surgical instrument according to claim 1, further comprising:
a fixing mechanism configured to hold the first abutment surface to the distal end resection surface.

3. The surgical instrument according to claim 2, wherein the fixing mechanism comprises
a fixing pin configured to be inserted into the femur, and
a pin hole that is provided as a through hole passing through the distal body portion and into which the fixing pin is inserted,
wherein the first abutment surface of the surgical instrument is configured to be held to the distal end resection surface through insertion of the fixing pin into the pin hole and into the femur.

4. The surgical instrument according to claim 3, wherein the pin hole is a plurality of pin holes that pass through the distal body portion in directions different from each other.

5. The surgical instrument according to claim 1, wherein at least one of the distal body portion and the spacer comprises a magnetic body, and the spacer is detachably attached to the distal body portion with a magnetic force.

6. The surgical instrument according to claim 1, wherein the distal body portion comprises a magnet, and
the spacer comprises a ferromagnetic body, and is detachably attached to the distal body portion with a magnetic force.

7. The surgical instrument according to claim 1, wherein the spacer is a plurality of additional spacers having thicknesses different from each other.

8. An artificial knee joint replacement apparatus comprising the surgical instrument of claim 1 that is configured for bone re-resection for installing a femur side component.

9. The surgical instrument according to claim 1, wherein when the spacer is in position and displacing the holding position of the first abutment surface with respect to the distal end resection surface, the spacer extends beyond the distal end resection surface.

10. The surgical instrument according to claim 1, wherein the spacer is detachably attached to the distal body portion at the first abutment surface and configured to abut against the distal end resection surface, the spacer including a flat plate shape with a front surface and a rear surface formed parallel to the front surface.

* * * * *